(12) United States Patent
Bednarek et al.

(10) Patent No.: US 6,447,507 B1
(45) Date of Patent: Sep. 10, 2002

(54) RAIL CATHETER ABLATION AND MAPPING SYSTEM

(75) Inventors: Michael C. Bednarek, Buffalo, MN (US); John F. Swartz, Tulsa, OK (US); Michael J. Coyle; John D. Ockuly, both of Minnetonka, MN (US); James A. Hassett, Bloomington, MN (US)

(73) Assignee: Daig Corporation, Minnetonka, MN (US)

(*) Notice: Subject to any disclaimer, the term of this patent is extended or adjusted under 35 U.S.C. 154(b) by 0 days.

(21) Appl. No.: 09/498,139

(22) Filed: Feb. 4, 2000

Related U.S. Application Data

(62) Division of application No. 08/968,414, filed on Nov. 12, 1997, now Pat. No. 6,120,500.

(51) Int. Cl.⁷ .................. A61B 18/14; A61B 5/042; A61N 1/05
(52) U.S. Cl. .................. 606/41; 600/374; 607/99; 607/105; 607/113; 607/122
(58) Field of Search .................. 606/41, 47, 49; 607/99, 105, 113, 122; 600/374

(56) References Cited

U.S. PATENT DOCUMENTS 6,048,329 A * 4/2000 Thompson et al. ......... 607/122

* cited by examiner

Primary Examiner—Lee Cohen
(74) Attorney, Agent, or Firm—Scott R. Cox

(57) ABSTRACT

An ablation system for ablating cardiac tissue within a chamber of the human heart including a guiding introducer system, a rail, one end of which is contained within the guiding introducer system, and an ablation catheter system which is supported by the guiding introducer system. The guiding introducer system may be a single or multiple guiding introducers. The ablation system may include a slotted sheath which passes over the rail which supports the ablation catheter. A process is disclosed for ablation of cardiac tissue to form a linear lesion utilizing a rail catheter ablation and mapping system which includes a guiding introducer, a rail and an ablation catheter system advanced over the rail.

17 Claims, 13 Drawing Sheets

RAIL CATHETER ABLATION AND MAPPING SYSTEM

This application is a divisional of copending application(s) application No. 08/968,414 filed on Nov. 12, 1997, now U.S. Pat. No. 6,120,500

FIELD OF INVENTION

This invention relates to a rail catheter ablation and mapping system designed to map and ablate specific locations within chambers of a human heart. In addition, it relates to a process for mapping and ablating cardiac tissue utilizing a rail catheter ablation and mapping system to form linear lesions within chambers of a human heart.

BACKGROUND

Catheters have been in use for medical procedures for many years. Catheters can be used for medical procedures to examine, diagnose and treat while positioned at a specific location within the body which is otherwise inaccessible without more invasive procedures. During these procedures a catheter is inserted into a vessel located near the surface of a human body and is guided to a specific location within the body for examination, diagnosis and treatment. For example, one procedure utilizes a catheter to convey an electrical stimulus to a selected location within the human body. Another procedure utilizes a catheter with sensing electrodes to monitor various forms of electrical activity in the human body.

Catheters are used increasingly for medical procedures involving the human heart. Typically, the catheter is inserted in an artery or vein in the leg, neck or arm of the patient and threaded, sometimes with the aid of a guidewire or introducer, through the vessels until a distal tip of the catheter reaches the desired location for the medical procedure in the heart.

A typical human heart includes a right ventricle, a right atrium, a left ventricle and a left atrium. The right atrium is in fluid communication with the superior vena cava and the inferior vena cava. The atrioventricular septum separates the right atrium from the right ventricle. The tricuspid valve contained within the atrioventricular septum provides communication between the right atrium and the right ventricle. On the inner wall of the right atrium, where it is connected with the left atrium, is a thin-walled, recessed portion, the fossa ovalis. Medical procedures are frequently performed in the left atrium using transseptal procedures performed through the interatrial septum. Present in the wall of the left atrium are the entrances to the four pulmonary veins: the right superior, the left superior, right inferior and left inferior pulmonary veins. The mitral valve contained in the atrioventricular septum provides communication between the left atrium and the left ventricle.

In the normal heart, contraction and relaxation of the heart muscle (myocardium) takes place in an organized fashion as electro-chemical signals pass sequentially through the myocardium from the sinoatrial (SA) node to the atrioventricular (AV) node and then along a well defined route which includes the His-Purkinje system into the left and right ventricles.

Sometimes abnormal rhythms occur in the heart which are referred to generally as arrhythmia. Abnormal arrhythmias which occur in the atria are referred to as atrial arrhythmia. Three of the most common atrial arrhythmia are ectopic atrial tachycardia, atrial fibrillation and atrial flutter. Atrial fibrillation is the most common of all sustained cardiac arrhythmias. While it is present in less than one percent of the general population, it has been estimated that at least 10 percent of the population over 60 is subject to atrial fibrillation. Although frequently considered to be an innocuous arrhythmia, atrial fibrillation can result in significant patient discomfort and even death because of a number of associated problems, including: an irregular heart rate which causes patient discomfort and anxiety, loss of synchronous atrioventricular contractions which compromises cardiac hemodynamics resulting in varying levels of congestive heart failure, and stasis of blood flow, which increases the likelihood of thromboembolism.

Efforts to alleviate these problems in the past have included significant usage of pharmacological treatments. While pharmacological treatments are sometimes effective, in some circumstances drug therapy has had only limited effectiveness and is frequently plagued with side effects, such as dizziness, nausea, vision problems and other difficulties.

An increasingly common medical procedure for the treatment of certain types of cardiac arrhythmia is catheter ablation. The use of catheters for ablating specific locations within the heart has been disclosed, for example in U.S. Pat. Nos. 4,641,649, 5,263,493, 5,231,995, 5,228,442 and 5,281,217.

The use of RF energy with an ablation catheter contained within a transseptal sheath for the treatment of W-P-W in the left atrium is disclosed in Swartz, J.F. et al. "Radiofrequency Endocardial Catheter Ablation of Accessory Atrioventricular Pathway Atrial Insertion Sites" *Circulation* Vol. 87, pgs. 487–499 (1993).

Ablation of a specific location within the heart requires the precise placement of the ablation catheter within the heart. One procedure used to place ablation catheters at a specific location in the heart utilizes a guiding introducer or a pair of guiding introducers. Ablation procedures using guiding introducers for treatment of atrial arrhythmia have been disclosed in U.S. Pat. Nos. 5,497,774, 5,427,119, 5,575,166, 5,640,955, 5,564,440 and 5,628,316. Lesions are produced in the heart tissue as an element of these procedures.

Placement of catheters at particular locations in a human body is sometimes accomplished using guide wires. For example, U.S. Pat. No. 5,163,911 discloses a catheter system utilizing a guidewire to guide a working catheter within the vasculature to perform medical procedures. U.S. Pat. No. 5,209,730 discloses an over-the-wire balloon dilation catheter for use within a vessel of the heart. A similar extendable balloon on a wire catheter system is disclosed in U.S. Pat. No. 5,338,301.

A different type of ablation catheter is disclosed in U.S. Pat. No. 5,482,037, which discloses an electrode catheter for insertion into a cavity of the heart. U.S. Pat. Nos. 5,487,385 and 5,575,810 disclose ablation systems which are utilized for mapping and ablation procedures within the right atria of the heart.

Conventional ablation procedures utilize a single distal electrode secured to the tip of an ablation catheter. Increasingly, however, cardiac ablation procedures utilize multiple electrodes affixed to the catheter body.

The ablation catheters commonly used to perform these ablation procedures produce scar tissue at particular points in the cardiac tissue by physical contact of the cardiac tissue with an electrode of the ablation catheter. One difficulty in obtaining an adequate ablation lesion using conventional ablation catheters is the constant movement of the heart, especially when there is an erratic or irregular heart beat. Another difficulty in obtaining an adequate ablation lesion is caused by the inability of conventional catheters to obtain and retain uniform contact with the cardiac tissue across the entire length of the ablation electrode surface. Without such continuous and uniform contact, any ablation lesions formed may not be adequate.

Effective ablation procedures are sometimes quite difficult because of the need for an extended linear lesion, sometimes as long as about 3 inches to 5 inches (approximately 8 cm. to 12 cm.). To produce such a linear lesion of this length within an erratically beating heart is a difficult task.

One process for the production of linear lesions in the heart by use of an ablation catheter is disclosed in U.S. Pat. Nos. 5,487,385, 5,582,609 and 5,676,662. In addition, a process for the production of a series of linear lesions in the atria for the treatment of atrial arrhythmia is disclosed in U.S. Pat. No. 5,575,766.

To form linear lesions within the heart using a conventional ablation tip electrode requires the utilization of procedures such as a "drag burn". During this procedure, while ablating energy is supplied to the ablating electrode, the ablating electrode is drawn across the tissue to be ablated, producing a line of ablation. Alternatively, a series of points of ablation are formed in a line created by moving the ablating electrode incremental distances across the cardiac tissue. The effectiveness of these procedures depends on a number of variables including the position and contact pressure of the ablating electrode of the ablation catheter against the cardiac tissue, the time that the ablating electrode of the ablation catheter is placed against the tissue, the amount of coagulum that is generated as a result of heat generated during the ablation procedure and other variables associated with a beating heart, especially an erratically beating heart. Unless an uninterrupted track of ablated cardiac tissue is created, unablated cardiac tissue or incompletely ablated cardiac tissue may remain electrically active, permitting the continuation of the reentry circuit which causes the arrhythmia. Thus, new devices are necessary for the production of linear lesions in the heart.

SUMMARY OF INVENTION

The present invention is a rail catheter ablation and mapping system for ablation procedures in the human heart which, in a preferred embodiment, includes an inner and an outer guiding introducer, a rail, an ablation catheter, and a slotted sheath. One end of the rail is secured to the outer guiding introducer. The rail is advanced out of the guiding introducers. The ablation catheter is extended through a lumen of the slotted sheath. The slotted sheath with ablation catheter inside is extended from the guiding introducers over the rail to form a loop to map and ablate cardiac tissue.

Also disclosed is a rail catheter ablation and mapping system which includes a single guiding introducer, a rail, a slotted sheath, and an ablation catheter. One end of the rail is secured to the guiding introducer. The rail is advanced out of the guiding introducer. The ablation catheter is extended through a lumen of the slotted sheath. The slotted sheath with ablation catheter inside is extended from the guiding introducer over the rail to form a loop to map and ablate cardiac tissue.

The ablation procedures may be performed by use of an ablation catheter containing a single electrode which may be formed from a series of coils. As an alternative, the ablation catheter includes a series of electrodes. Either of these ablation catheters preferably performs the ablation procedure through slots of the slotted sheath with a flushing system utilized within the slotted sheath and/or within the ablation catheter to cool and flush the electrode during the ablation procedure.

Also disclosed is a rail catheter ablation and mapping system which includes a guiding introducer system, a rail, and an ablation catheter which includes one or more electrodes contained in a lumen of the ablation catheter. A plurality of openings are provided in the surface of the ablation catheter. A system for introduction of a conductive media through the lumen of the ablation catheter is also provided which passes the conductive media through the openings to conduct the ablating energy to the tissue to be ablated.

Also disclosed is a rail catheter ablation and mapping system which includes a guiding introducer system, a rail and an ablation catheter with flexible electrodes.

A process for ablation of cardiac tissue to form linear lesions in a chamber of a human heart is also disclosed. During the procedure, a guiding introducer system, with a rail secured to the guiding introducer, is advanced through the vasculature of the human body into the chamber of the heart. The rail is extended from the guiding introducer. A slotted sheath is then extended through a lumen of the guiding introducer over the rail. The ablation catheter passes through a lumen in the slotted sheath. As the slotted sheath containing an ablation catheter passes over the surface of the cardiac tissue, it maps and/or ablates the cardiac tissue.

DETAILED DESCRIPTION OF THE PREFERRED EMBODIMENT

Figure 1:
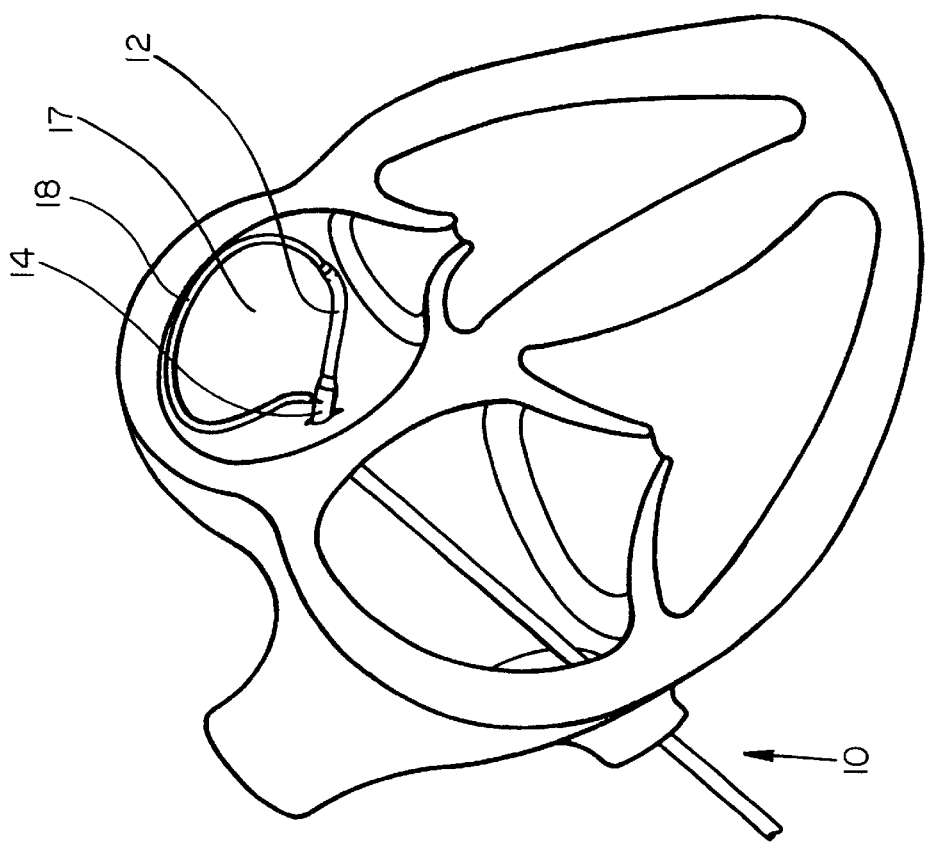
FIG. 1 is a cutaway view of a human heart showing the rail catheter ablation and mapping system in use about an inner surface of the left atrium.
Figure 2:
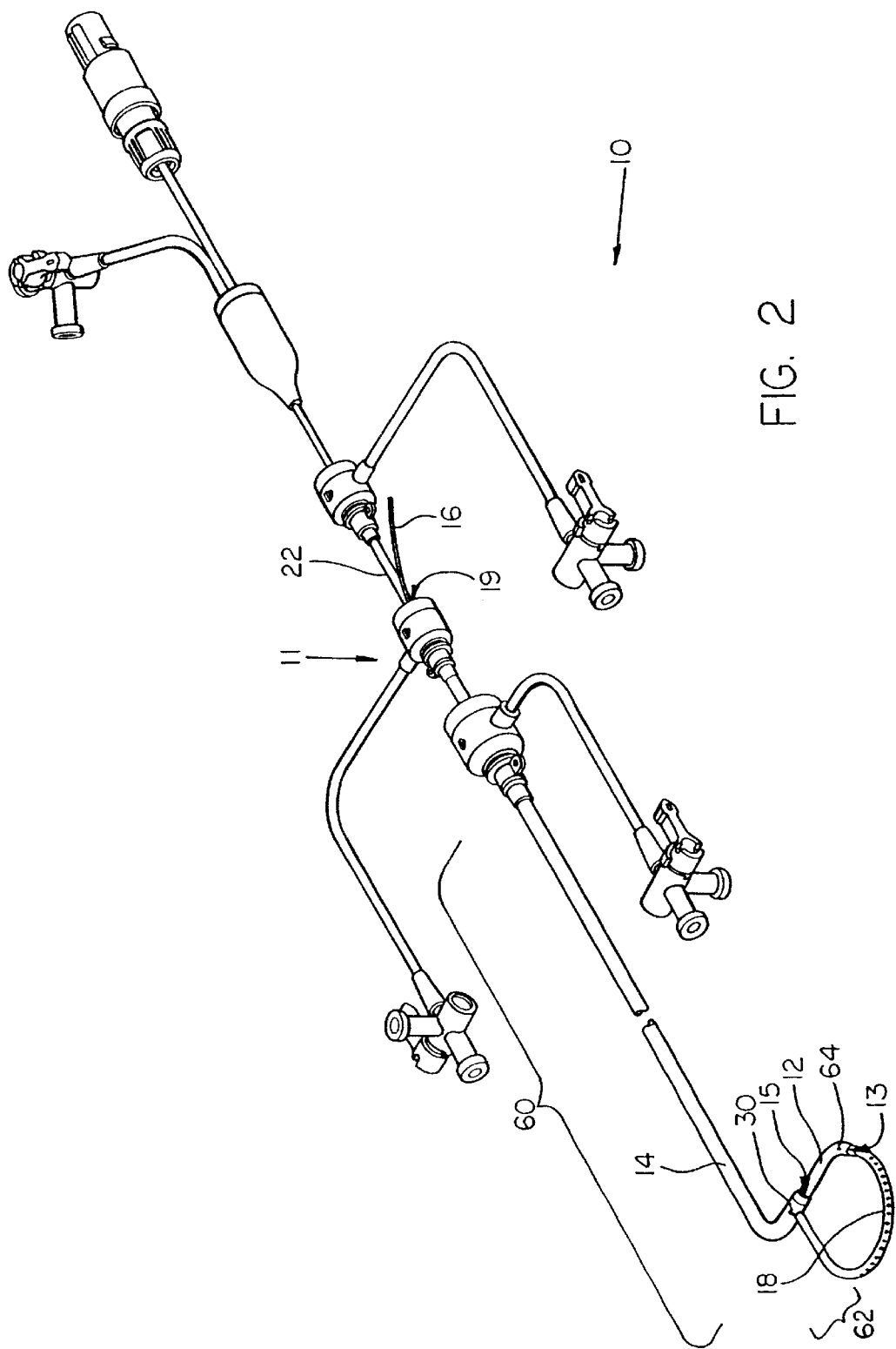
FIG. 2 is a perspective view of the first embodiment of the rail catheter ablation and mapping system containing an inner and outer guiding introducer and a slotted sheath with the ablation catheter extending from the distal tip of the inner guiding introducer.
Figure 3:
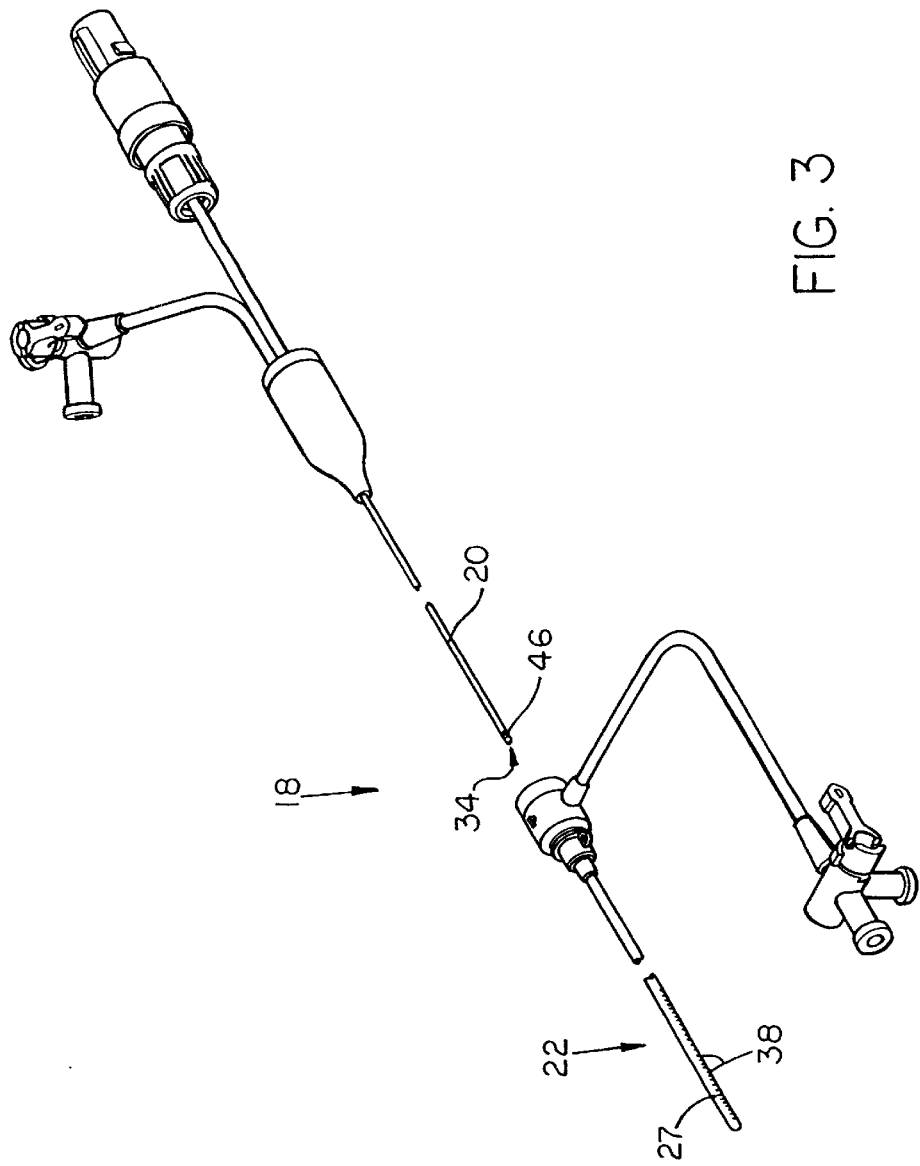
FIG. 3 is a perspective, exploded view of an ablation catheter with tip electrode utilized with the slotted sheath of the rail catheter ablation and mapping system of FIG. 2.
Figure 11:
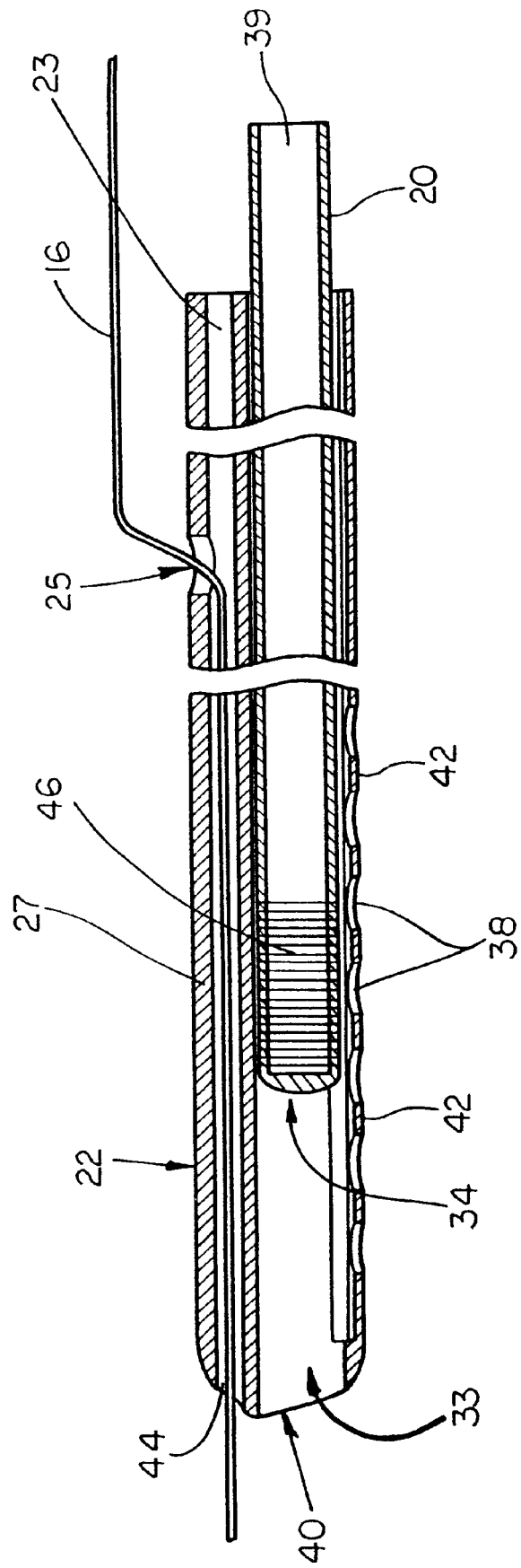
FIG. 11 is a side cutaway view of a portion of the slotted sheath and ablation catheter of the rail catheter ablation and mapping system of FIG. 2 which contains the ablation catheter with coiled electrode and a portion of the rail.

The rail catheter ablation and mapping system (10) of the present invention as shown in FIGS. 1 and 2 includes a guiding introducer system (11), comprising preferably an inner guiding introducer (12) and an outer guiding introducer (14), each with proximal and distal ends and each containing a lumen (13, 15) extending lengthwise substantially through each of the guiding introducers, a rail (16), and an ablation system (18) passing through the lumen (13) of the inner guiding introducer (12). In the first embodiment of the invention, as shown in FIGS. 3 and 11, the ablation system (18) consists of an ablation catheter (20) passing through a lumen (33) of a slotted sheath (22).

Figure 4:
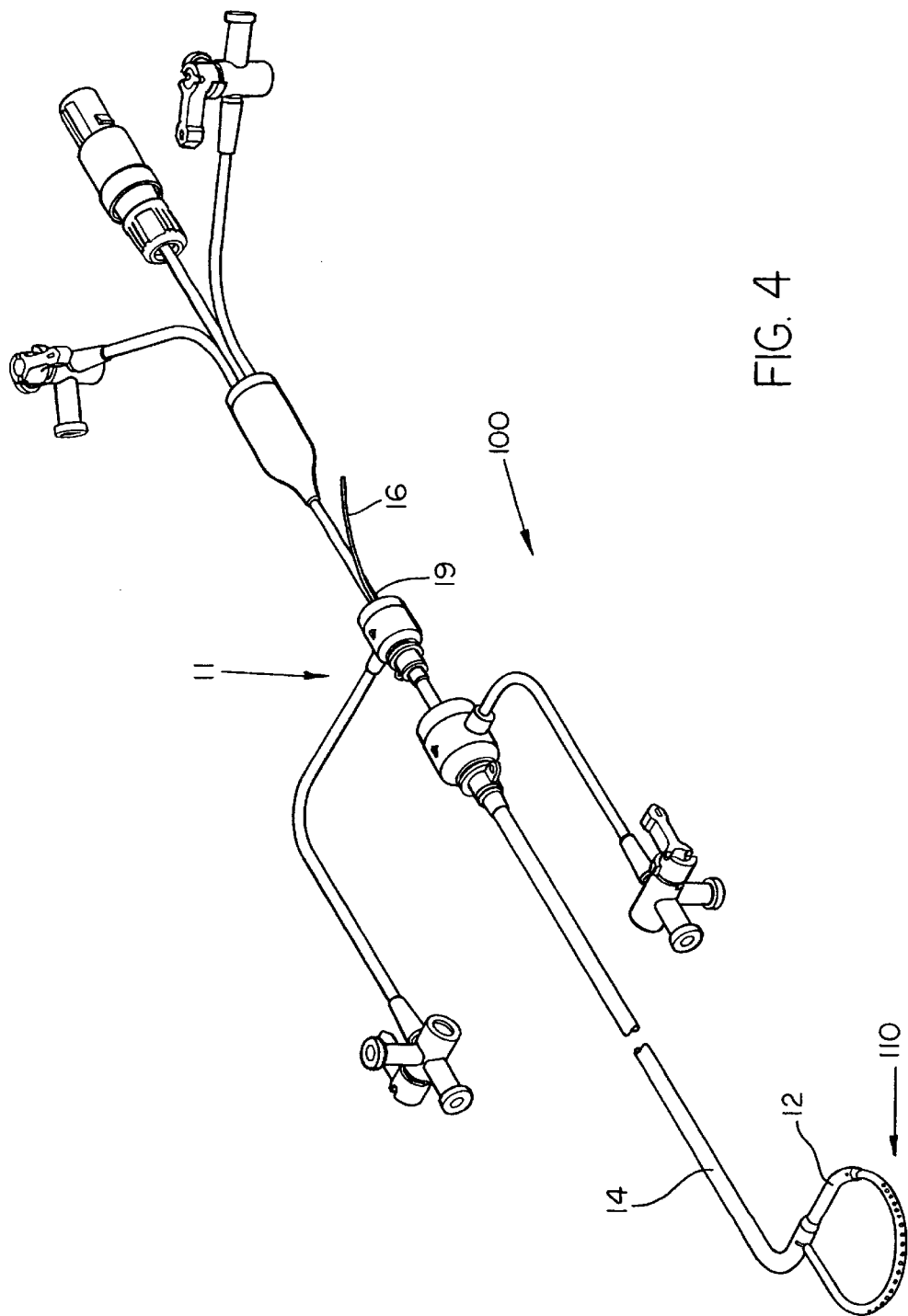
FIG. 4 is a perspective view of a second embodiment of the rail catheter ablation and mapping system showing an inner and outer guiding introducer and an ablation catheter extending from the distal tip of the inner guiding introducer.
Figure 5:
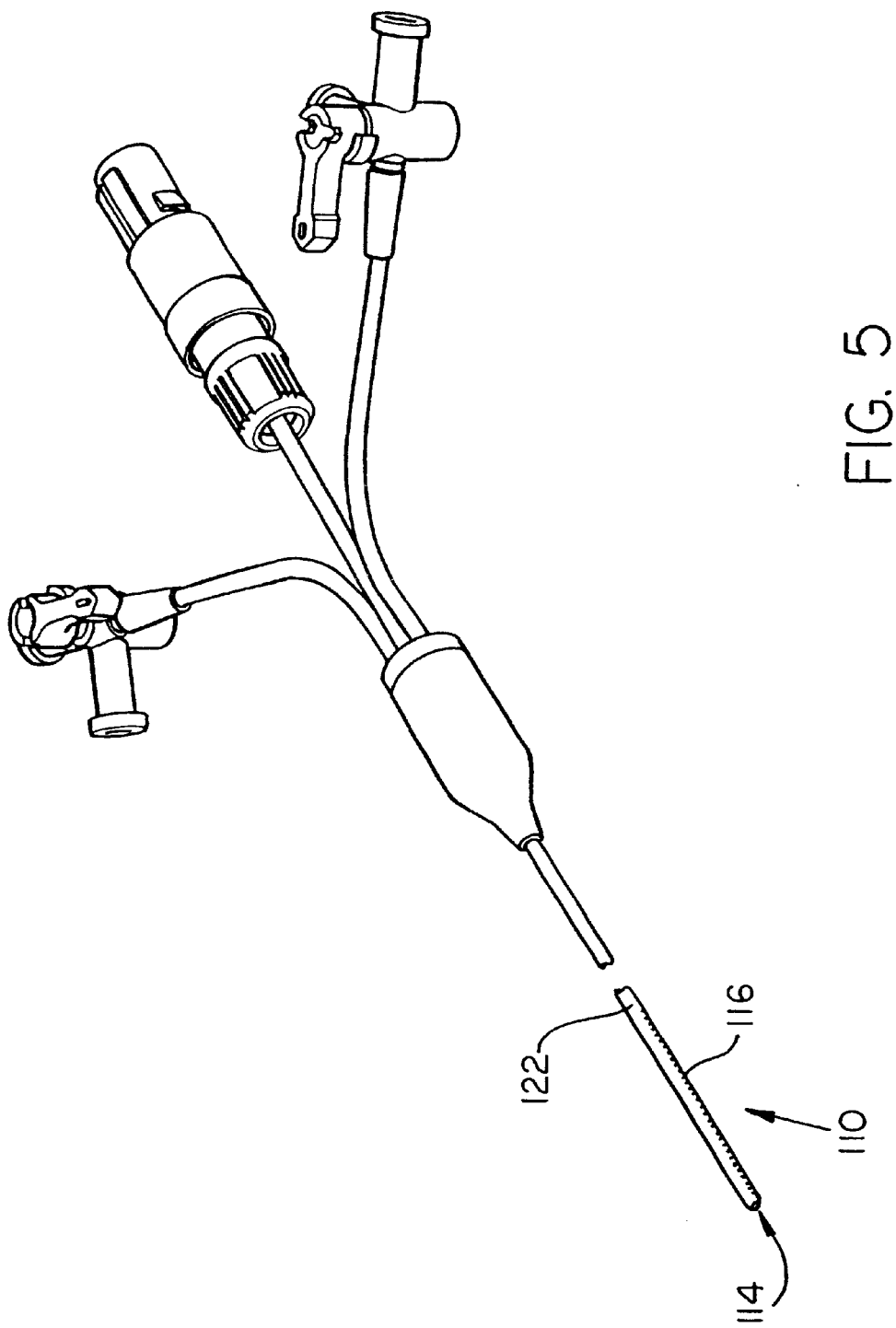
FIG. 5 is a perspective view of the ablation catheter of the rail catheter ablation and mapping system of FIG. 4.
Figure 6:
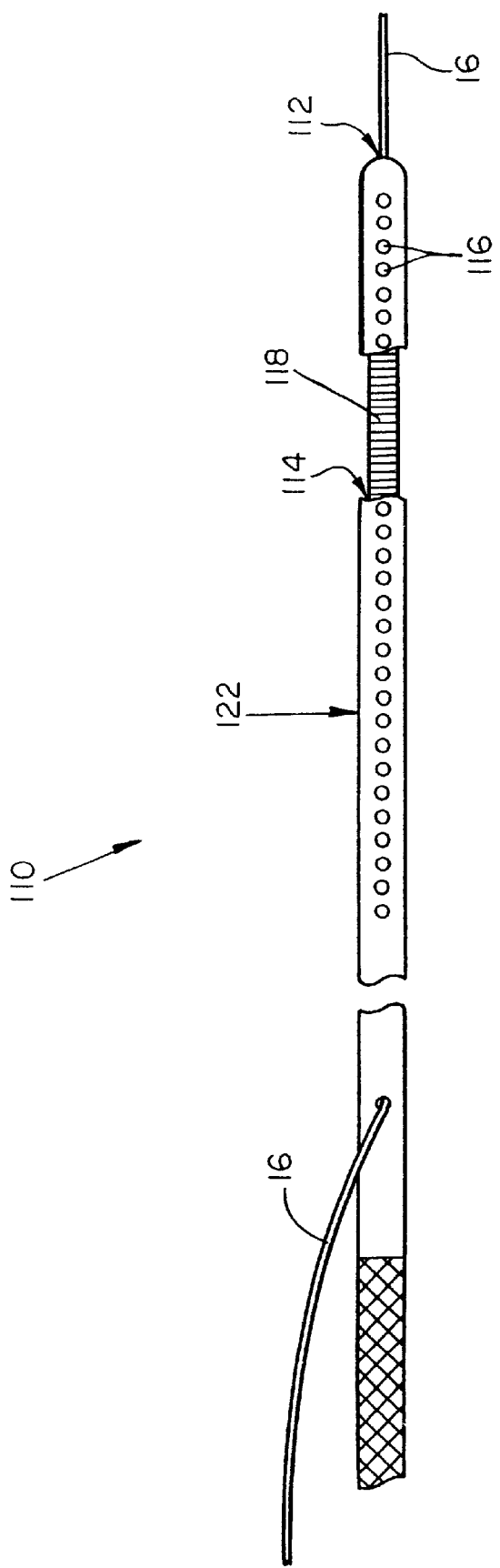
FIG. 6 is a side cutaway view of the ablation catheter of FIG. 5.

In a second embodiment of the present invention, as shown in FIGS. 4, 5 and 6, the rail catheter ablation and mapping system (100) includes a guiding introducer system (102), which is preferably an inner guiding introducer (104) and an outer guiding introducer (106), a rail (108), and an ablation catheter (110) containing at least two lumens (112, 114). The ablation catheter (110) includes a plurality of openings (116) through the surface (122) of the ablation catheter (110), an electrode (118) contained within one of the lumen (114) of the ablation catheter (110) and a system (not shown) for introduction of a conductive media into one of the lumen (114) of the ablation catheter (110).

Figure 7:
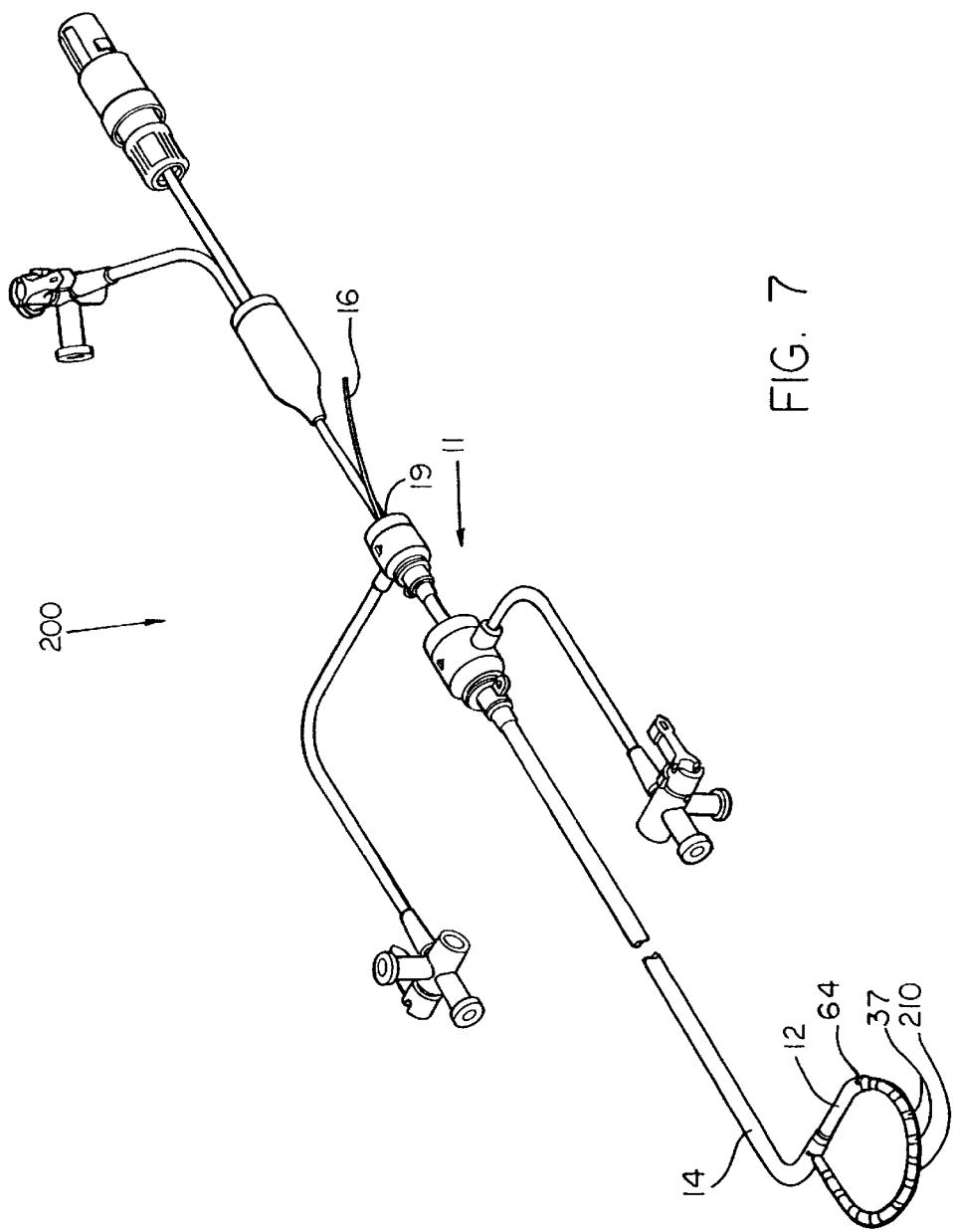
FIG. 7 is a perspective view of a third embodiment of the rail catheter ablation and mapping system containing an inner and outer guiding introducer, a rail, and an ablation catheter containing a plurality of electrodes, which catheter extends from the distal tip of the inner guiding introducer.
Figure 10:
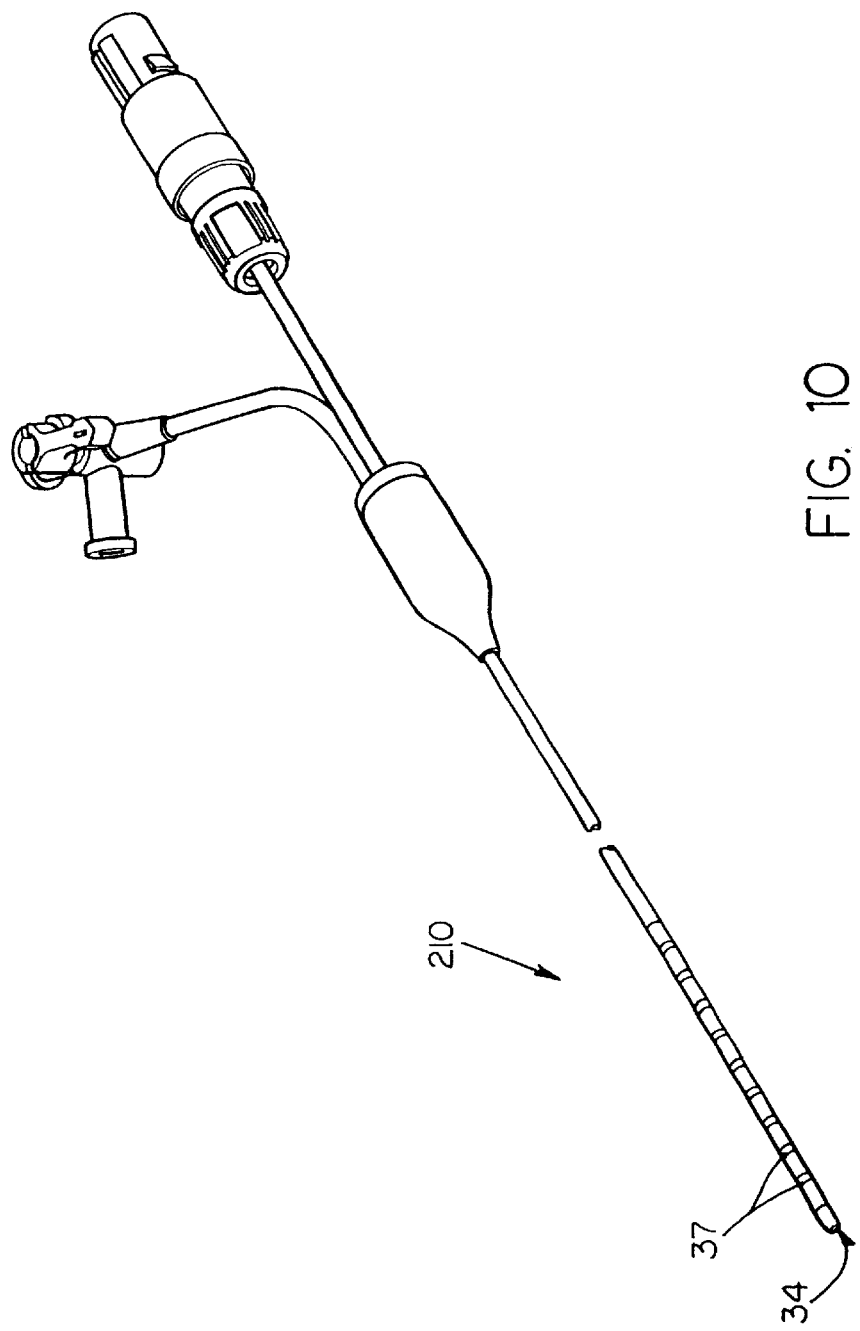
FIG. 10 is a perspective view of an ablation catheter of the rail catheter ablation and mapping system of FIG. 7 containing multiple electrodes.

In a third alternative embodiment, as shown in FIGS. 7 and 10, the rail catheter ablation and mapping system (200) includes a guiding introducer system (202), which is preferably an inner guiding introducer (204) and outer guiding introducer (206), a rail (208), and an ablation catheter (210) which passes over rail (208).

Figure 8:
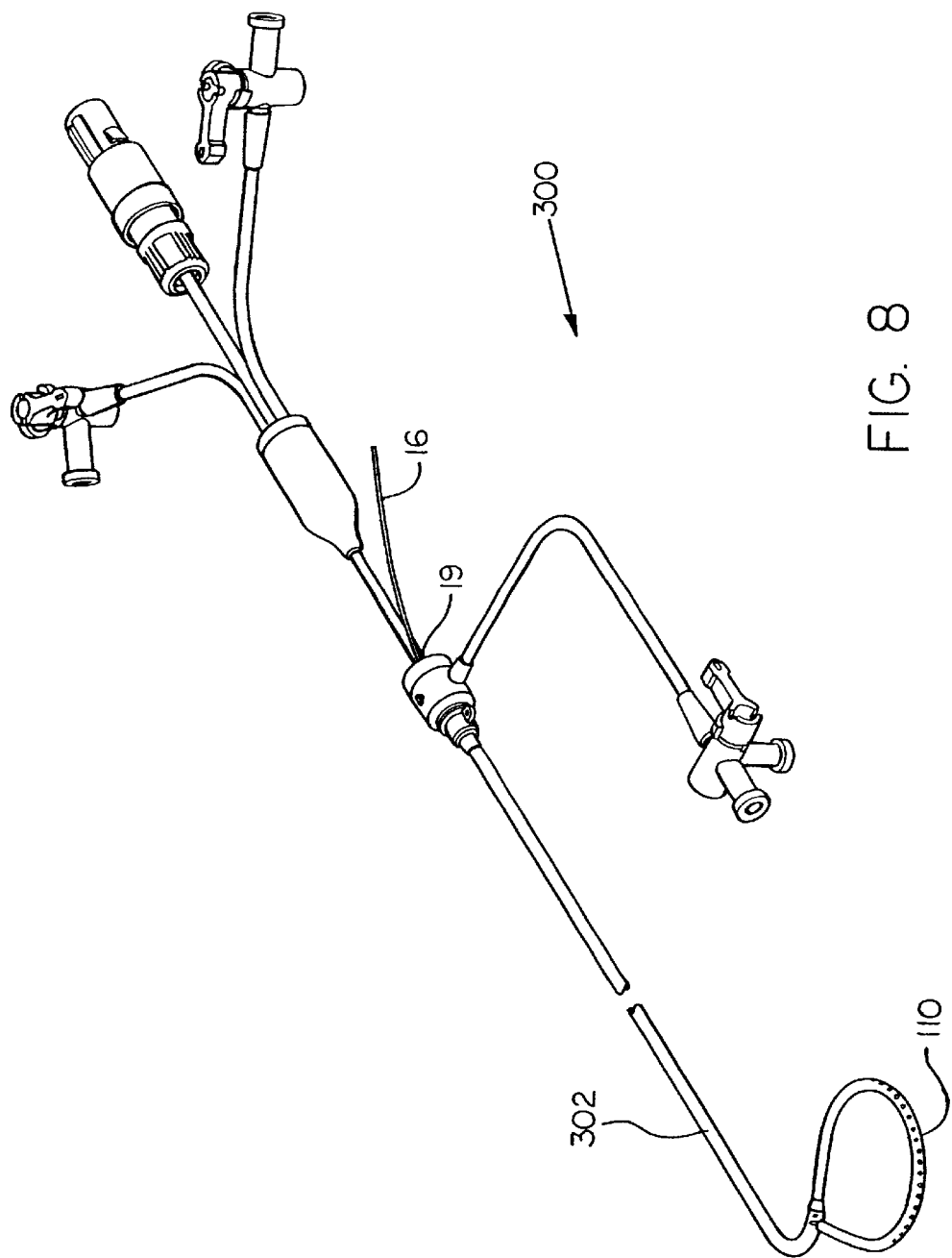
FIG. 8 is a perspective view of a fourth embodiment of the rail catheter ablation and mapping system disclosing a single guiding introducer, an ablation catheter extending from the distal tip of the guiding introducer, and a rail.

In a fourth alternative embodiment shown in FIG. 8, the rail catheter ablation and mapping system (300) includes a single guiding introducer (302), a rail (304), and an ablation catheter system (306) which passes over the rail (304).

The introducer or introducers utilized with the rail catheter systems of the present invention can be any conventional guiding introducer with a sufficient inner diameter to accommodate the rail catheter ablation system and introduce the ablation system into a chamber of the human heart in which the ablation procedure is to be performed, preferably the left atrium (17), as shown in FIG. 1. In a preferred embodiment, the introducers are precurved inner and outer guiding introducers, such as those sold by Daig Corporation under the names AMAS 1-2 outer and AMAS 3-4 inner.

Medical practitioners normally monitor the introduction of a catheter and its progress through the vascular system by fluoroscope. However, such fluoroscopes do not easily identify the specific features of the heart in general and the particular structures of individual chambers of the human heart in specific, thus making placement of the rail catheter ablation and mapping systems (10, 100, 200, 300) within the heart difficult. Placement is also complicated when the heart is beating resulting in the ablation system (18, 110, 210) moving within the chamber as blood is pumped through the heart throughout the procedure. Utilization of preferably a precurved inner guiding introducer and precurved outer guiding introducer, with the rail catheter ablation systems (18, 110, 210) makes placement of the ablation system at the correct location in the heart is made easier. In addition, use of the rail catheter ablation and mapping systems (10, 100, 200, 300) results in more positive tissue contact which permits the formation of better ablation lesions.

In a preferred embodiment, as shown in FIGS. 1 and 2, an inner and outer guiding introducer (12, 14) are used in combination. When using an inner (12) and outer (14) guiding introducer, the outer diameter of the inner guiding introducer (12) is generally only slightly smaller than the inner diameter of the outer guiding introducer (14) so that the two introducers can be used together. In a preferred embodiment, the rail (16) passes between the inner (12) and outer (14) guiding introducers. Thus, the difference in diameter between the inner diameter of the outer guiding introducer (14) and the outer diameter of the inner guiding introducer (12) must be sufficient to accommodate the rail (16) without interfering with the operation of the guiding introducer system (11). In a preferred embodiment, the difference in diameter should be between 1 and 3 French (one French unit equals ⅓ of a millimeter), about 0.01 inch to about 0.04 inch (about 0.3 mm. to about 1 mm.).

By utilizing different curvatures for the distal portions (62) of the inner (12) and outer (14) guiding introducer and by rotating and extending the inner guiding introducer (12) in relation to the outer guiding introducer (14), the overall shape of the guiding introducer system (11) can be modified to support the ablation system (18). Not only can the use of a pair of guiding introducers (12, 14) in combination provide varying overall shapes for the guiding introducer system (11) than when using a single guiding introducer, but the use of a pair of guiding introducers (12, 14) is also helpful in the operation of the rail (16), as will be discussed in more detail. When a pair of introducers (12, 14) are utilized, in one preferred embodiment when the ablation procedure is performed transseptally in the left atrium, the preferred inner (12) and outer (14) guiding introducers are AMAS 1-2 outer introducer and AMAS 3-4 inner introducer, produced by Daig Corporation.

In an alternative embodiment, instead of utilizing an inner (12) and outer (14) guiding introducer of the guiding introducer system (11), a single precurved guiding introducer (302) can be utilized as an element of the rail catheter ablation and mapping system (300), as shown in FIG. 8.

Figure 9:
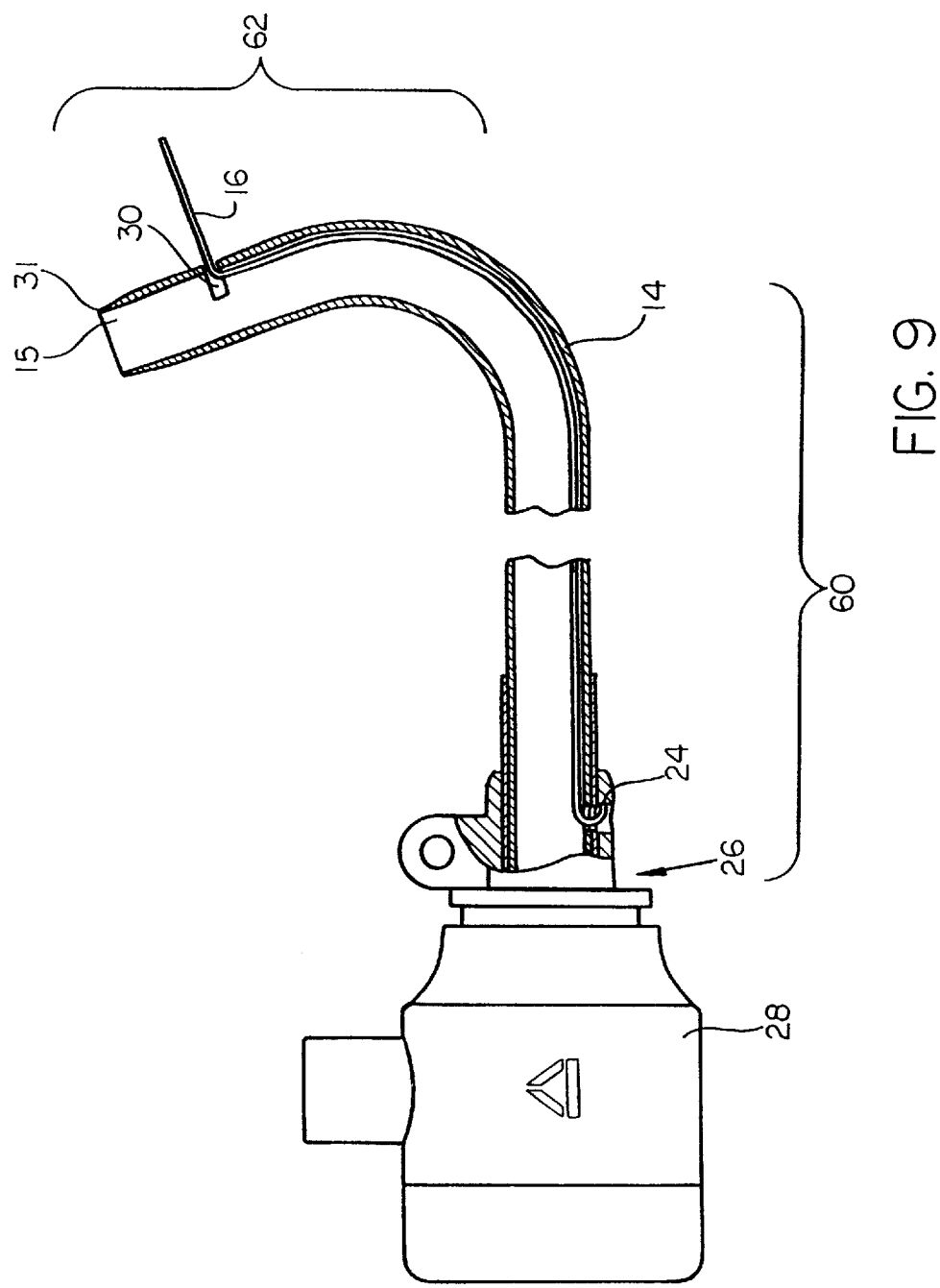
FIG. 9 is a cutaway side view of the outer guiding introducer and rail of the rail catheter ablation and mapping system of FIG. 2, with the rail secured near the proximal end of the outer guiding introducer.

The guiding introducers utilized with the guiding introducer system contain a first section (60) as shown in FIGS. 2 and 9 which is generally an elongated, hollow straight section of sufficient length for introduction in the patient and for manipulation from the point of insertion to the specific desired location within the heart. Continuous with the distal end of this first section of the guiding introducer is a precurved, distal portion (62) of the guiding introducer as shown in FIGS. 2 and 9. The choice of curvature of this precurved distal portion depends on the choice of location within the heart for the ablation procedure. For example, when the ablation procedure occurs in the left atrium using a transseptal approach, the preferred guiding introducers are AMAS guiding introducers manufactured by Daig Corporation. The overall curvature of the various guiding introducers can be modified by use of various straight or curved sections to achieve the desired shape for the guiding introducers. In addition, the choice of the guiding introducer or guiding introducer system can be modified to place the rail catheter ablation and mapping system (10, 100, 200, 300) at various locations within the chambers of the heart. Examples of acceptable guiding introducers are those disclosed, for example, in U.S. Pat. Nos. 5,427,119, 5,497,774, 5,575,766, 5,640,955, 5,564,440, 5,628,316, and 5,656,028, as well as other precurved guiding introducers sold by Daig Corporation.

An important design feature of the guiding introducer (302) or pair of guiding introducers (12, 14) when used for an ablation procedure is that they provide a stable platform supported by the cardiac anatomy to permit the ablation system (18, 110, 210) and the rail (16) to be extended from the guiding introducer (302) or inner and outer guiding introducers (12, 14) to circumscribe the inner surface of the chamber of the heart in which the medical procedure occurs. The guiding introducer (302) or pair of guiding introducers (12, 14) also provide stable support for the ablation system (18, 110, 210) to perform the ablation procedure within the heart without the need for repeated repositioning.

The distal tip of the guiding introducers may be, and generally are, tapered to form a good transition with a dilator.

The guiding introducers may be made of any material suitable for use in humans, which has a memory or permits distortion from, and subsequent substantial return to, the desired three dimensional or complex multi-planar shape. For purpose of illustration and not limitation, the internal diameter of the guiding introducers may vary from about 6 to about 14 French (about 0.07 inch to about 0.20 inch) (about 2.0 mm. to about 5.0 mm.). Such guiding introducers can accept dilators from about 6 to about 14 French (0.07 inch to about 0.20 inch) (about 2.0 mm. to about 5.0 mm.) and appropriate guide wires. Obviously, if larger or smaller dilators and catheters are used in conjunction with the guiding introducers of the present invention, modification can be made in the size of the guiding introducers.

The guiding introducer (12) preferably also contains one or a plurality of radiopaque tip marker bands near the distal tip. Various modifications may be made in the shapes by increasing or decreasing the size of the tip markers or adding additional tip markers.

The guiding introducer (12) also preferably contains one or a plurality of vents (64) near the distal tip of the guiding introducers, preferably 3 or 4 vents, as shown in FIGS. 2 and 7. The vents are preferably located no more than about 2 to about 3 inches (about 5 cm. to about 8 cm.) from the distal tip of the guiding introducers and more preferably about 0.1 inch to about 2.0 inches (about 0.2 cm. to about 5.0 cm.) from the distal tip. The size of the vents should be in the range of about 0.02 inch to about 0.06 inch (about 0.05 cm. To about 0.15 cm.) in diameter. The vents are generally designed to prevent air emboli from entering the guiding introducers due to the withdrawal of a catheter contained within the guiding introducers in the event the distal tip of one of the guiding introducers is occluded.

Variances in size and shape of the guiding introducers are also intended to encompass guiding introducers used with pediatric hearts. While pediatric ablation procedures are generally not performed on children less than about 2 years of age, under extreme situations, such ablation procedures may be conducted. These procedures may require reductions in the size and shape of the guiding introducers.

The configuration of the rail (16) is an important aspect of the invention. The purpose of the rail (16) is to provide a guide and support for the ablation system (18, 110, 210) while the ablation and/or mapping procedures are being performed within the chamber of the heart. To provide this support, the rail (16) must be flexible enough not to injure the inner surface of the chamber of the heart in which it is used, while still retaining sufficient structural integrity to support the ablation system (18, 110, 210) as it traverses around the inner surface of the chamber of the heart to perform the ablation procedure.

In order to achieve the preferred curvature and performance of the rail (16), in a preferred embodiment, the rail (16) is constructed of a super elastic metal alloy material, such as a nickel-titanium alloy, such as a NiTiNol® material. Such super elastic material is more preferably a shape memory alloy with a transformation temperature below that of the human body temperature. Alternatively, the shape memory alloy may also have a transformation temperature above that of the human body. In this alternative utilization, an electric current is applied to the shape memory alloy material to convert it into a super elastic state. When such super elastic, shape memory alloy is utilized, rail (16) retains its curvature when exiting the outer guiding introducer (14) through the slot or opening (30) near the distal end (31) of the outer guiding introducer (14), as shown in FIGS. 2 and 9, while still retaining sufficient flexibility to support the ablation system (18, 110, 210) as it circumscribes the inner surface of the heart chamber in which the ablation procedure is performed.

Figure 12A:
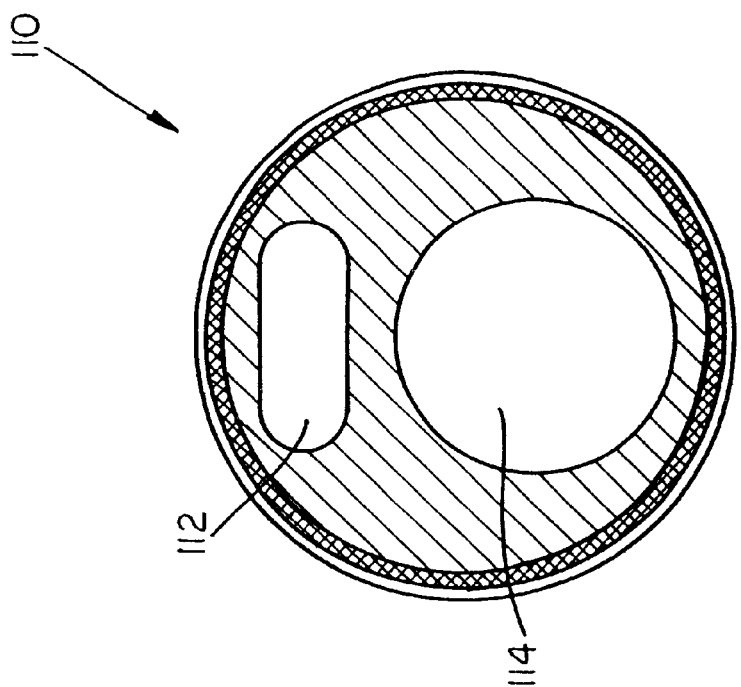
FIG. 12A is a cross-section of a proximal portion of the ablation catheter of FIG. 6 showing a pair of lumens.
Figure 12B:
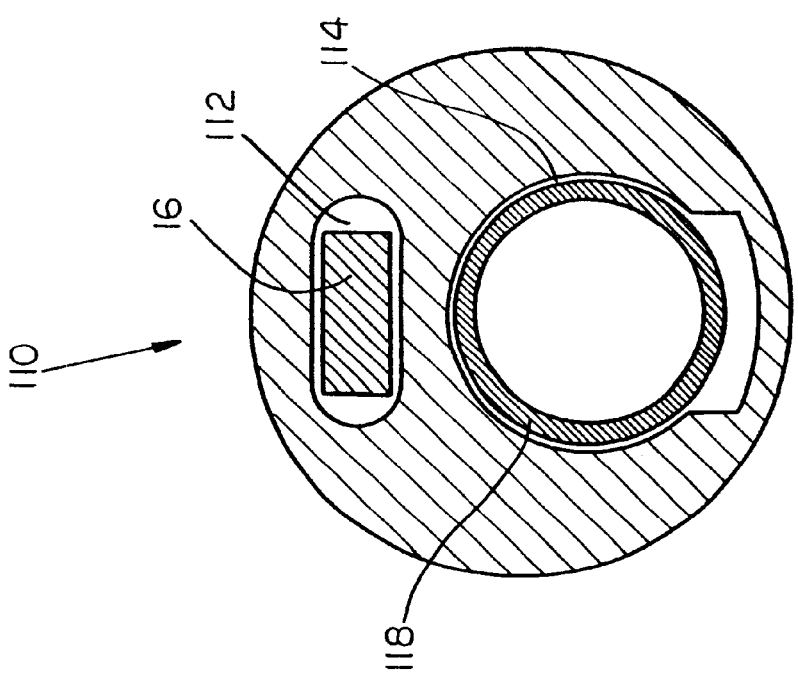
FIG. 12B is a cross-section of a distal portion of the ablation catheter of FIG. 6 showing a pair of lumens, one containing the rail and the second containing the electrode of the ablation catheter.

In a preferred embodiment, the cross section of the rail is preferably rectangular in shape, as shown in FIG. 12B. The rail (16) preferably is about 0.02 inch to about 0.04 inch (about 0.05 cm. to about 0.1 cm.) in width and from about 0.005 inch to about 0.02 inch (about 0.01 cm. to about 0.05 cm.) in thickness. As the preferred rail (16) is a flattened wire, it is resistant to bending laterally while still retaining sufficient flexibility to form a loop when extended away from the outer guiding introducer (14) by advancing the ablation system (18, 110, 210) over the rail (16). The rail (16) should be of sufficient length so that it can be fully extended into the chamber of the heart to be ablated and back out the proximal end of the guiding introducer system (11), exiting at point (19) as shown in FIG. 2. Thus, it should be at least about 60 inches (152 cm.) in length.

One end (24) of the rail (16) is preferably secured in place as shown in FIG. 9. The manner of securing end (24) of the rail (16) in place and the location where the rail (16) is secured is not critical. In one preferred embodiment, end (24) of the rail (16) is secured to the hub (28) at the proximal end (26) of the outer guiding introducer (14). End (24) of the rail (16) is secured in place by conventional means, such as with adhesives. Alternatively, one end of the rail (16) may be secured by conventional securing methods to one of the guiding introducers within a distal portion of the guiding introducer (not shown). In another alternative embodiment (not shown), neither end of the rail is secured in place and both ends pass through a lumen or lumens of the guiding introducer(s) and/or ablation system (18, 110, 210) and exit at the proximal end of the guiding introducer(s) and/or ablation system (18, 110, 210).

When end (24) of the rail (16) is secured in place at the proximal end (26) of the outer guiding introducer (14), as shown in FIG. 9, the remaining portion of the rail (16) extends through the lumen (15) of the outer guiding introducer (14) between the inside surface of the outer guiding introducer (14) and the outside surface of the inner guiding introducer (12) to a location near the distal end (31) of the outer guiding introducer (14). The rail (16) then exits through an opening or slot (30) provided in the surface of the outer guiding introducer (14). In a preferred embodiment, the opening or slot (30) extends at least about 20 degrees, and preferably as much as 180 degrees, around the circumference of the outer guiding introducer (14). Opening or slot (30) permits the rail (16) to be moved laterally in relation to the outer guiding introducer (14) to adjust the position of the ablation system (18, 110, 210) while in use in the heart.

In order to substantially circumscribe the inner surface of a chamber of a human heart, the rail (16), preferably is angled outwardly from the outer guiding introducer (14) at an angle of approximately 60 to 180 degrees and more preferably from about 80 to 100 degrees as it exits the outer guiding introducer (14) through the opening or slot (30) as shown in FIG. 9.

In a preferred embodiment, as shown in FIG. 9, the rail (16) extends through the lumen (15) of the outer guiding introducer (14), out the opening or slot (30) and then loops back through a lumen (23) within the slotted sheath (22) as shown in FIG. 11. However, the rail need not extend through the entire length of the slotted sheath (22) and may exit through the side of the slotted sheath (22) at a location (25) proximal from the distal end (40) of the slotted sheath (22). The rail then runs along the side of the ablation catheter (18, 110, 210) through the lumen (13) of the inner guiding introducer (12) until it exits the proximal end of the inner guiding introducer (12).

The ablation catheters (18, 110, 210) is preferably an elongated catheter made of materials suitable for use in humans, such as nonconductive polymers. Exemplary polymers used for the production of the catheter body include those well known in the art such as polyurethanes, polyether-block amides, polyolefins, nylons, polytetrafluoroethylene, polyvinylidene fluoride, and fluorinated ethylene propylene polymers and other conventional materials.

The ablation catheters (18, 110, 210) preferably are flexible near its distal end (34) for at least 7 inches (18 cm.). While the more proximal portion of the ablation catheters (18, 110, 210) are preferably stiffer than the distal end, the stiffness of the ablation catheters (18, 110, 210) may be consistent over their entire length. Enhanced stiffness is generally provided to the ablation catheters (18, 110, 210) by conventional catheter forming procedures, such as by braiding a portion of the ablation catheter (20), or by use of higher durometer catheter materials.

The ablation catheter (20) should be sufficiently flexible so that its distal portion can pass smoothly through the lumen (33) within the slotted sheath (22) as shown in FIG. 11. However, the ablation catheter (20) should also be sufficiently stiff so that it can be advanced through the lumen (33) of the slotted sheath (22) without undue difficulty.

The length of the ablation catheters (18, 110, 210) is preferably from about 20 to about 60 inches (about 50 cm. to about 150 cm.). The diameter of the catheter is within ranges known in the industry, preferably, from about 4 to 16 French (about 0.05 inch to about 0.2 inch) (about 1.3 mm to about 5.2 mm) and more preferably from about 6 to 8 French (about 0.07 to about 0.1 inch) (about 1.8 mm to about 2.4 mm).

There are several alternative ablation systems. The ablation catheter (210) may contain a series of ring electrodes (37), as shown in FIG. 7, without a tip electrode. This ablation catheter (210) is introduced over the rail (16) of the guiding introducer system (11), as shown in FIG. 7. Alternatively, the ablation system may consist of a conventional ablation catheter with a tip electrode (36) and a series of ring electrodes (37).

The ring electrodes (37) may be rigid or flexible, circumferential or directional. The body of the ablation catheter (210) preferably contains one or more lumens extending through the catheter body from its proximal end to or near its distal end. Preferably, sufficient lumens are present in the catheter body to accommodate wires for one or more sensing and/or ablating electrodes. Thermosensing devices, such as thermocouples (not shown), may also be attached to the ablation catheter (20).

Alternatively a single tip electrode (46) may be used. The ablating tip electrode (46) may be rounded and secured to the distal tip of the ablation catheter (20) by conventional means.

The preferred source for energy generated through the ablating electrodes is radiofrequency energy, although other sources for energy can also be utilized including direct current, laser, ultrasound and microwave. The electrodes may monitor electrical activity within the heart.

In an alternative embodiment, the ablating electrode of the ablation catheter may be a tip coil electrode (46) secured at or near the distal tip (34) of the ablation catheter (20), as shown in FIGS. 3 and 11. This coil electrode (46) is preferably at least about 0.15 inch (0.4 cm.) in length. It is preferably formed from wire coils with a cross-section of about 0.005 inch (0.013 cm.), which are secured to the outside surface of the ablation catheter (20) by conventional methods, such as adhesives. In order to cool the coil electrode (46) during use, cooling fluid is introduced through the lumen (33) of the slotted sheath (22) and the lumen (39) of the ablation catheter so that the fluid can flow around and through the coils of the coil electrode (46) while the ablation procedure is proceeding.

In a preferred embodiment, the ablation catheter (20) is advanced and withdrawn within lumen (33) of the slotted sheath (22) as shown in FIG. 11. The preferred slotted sheath (22) of the present invention is disclosed in application Ser. No. 08/757,832, filed Nov. 27, 1996, owned by the common assignee, which disclosure is incorporated herein by reference. Once the slotted sheath (22) is properly positioned over the rail (16) in the cardiac chamber as shown in FIG. 1, the ablation catheter (20) is advanced within the lumen (33) of the slotted sheath (22) to ablate the cardiac tissue to form an ablation track or lesion.

Openings (38) are provided in the body (27) of the slotted sheath (22) to form a longitudinal line extending from near the distal tip (40) of the slotted sheath (22) proximally as shown in FIGS. 3 and 11. The number of individual openings (38) provided in the body (27) of the slotted sheath (22) is at least 3. The overall length of the flexible portion of the body (27) of the slotted sheath (22) containing the openings (38) is generally about the same length as the desired linear lesion to be formed, preferably from about 3 inches to about 5 inches (approximately 8 cm. to about 12 cm.).

The openings (38) in the body (27) of the slotted sheath (22) are preferably from about 0.010 inch to about 0.050 inch (about 0.025 cm. to about 0.127 cm.) in diameter. The shape of the openings (38) is not critical, but preferably, they are longer than they are wide. Referring to FIG. 11, a bridge (42) of sheath material exists between individual openings (38). The width of the bridge (42) of material should not be greater than about 0.05 inch (approximately 0.2 cm.). Located at the distal tip (40) of the slotted sheath (22) is the opening (44) through which the rail (16) extends through the slotted sheath (22). The structure of the slotted sheath (22) should be sufficiently flexible so that it can circumscribe the inner surface of the chamber of the heart, as shown in FIG. 1, yet stiff enough to support the ablation catheter (20) and rail (16) contained within lumens (33, 23) of the slotted sheath (22).

In an alternative preferred embodiment, instead of using an ablation catheter (20) advanced within a slotted sheath (22), the rail catheter ablation and mapping system (100) may utilize an ablation catheter (110) such as is disclosed in application Ser. No. 08/897,300, filed Jul. 21, 1997, owned by the common assignee and incorporated herein by reference, as shown in FIG. 6. The ablation catheter (110) of this system (100) contains a plurality of lumens (112, 114), one lumen (112) of which is used to receive the rail (16) as shown in FIGS. 12A and 12B. One or more electrodes (118) are located within a lumen (114) of the ablation catheter (110). A series of openings (116) are provided in the outer surface (122) of the ablation catheter (110), which extend from the outer surface (122) into the lumen (114) containing the electrodes (118). A system (not shown) is provided for the introduction of a conductive media into the lumen (114), which media conductively contacts the electrode (118) and then passes out through the openings (116) in the surface (122) of the ablation catheter (110). The electrode (118) utilized in one preferred embodiment, as shown in FIG. 6, constitutes one or more coiled electrodes extending along the length of the lumen (114) inside the 5 ablation catheter (110). The conductive media is forced out of the openings (116) in the ablation catheter (110). The electrode (118) does not directly contact the cardiac tissue to be ablated. Instead, the conductive media conducts the energy, preferably radiofrequency energy, from the electrode (118) to the surface of the cardiac tissue to be ablated. As the impedance of the conductive media is maintained at a level less than that of the impedance of the cardiac tissue, the cardiac tissue will heat up as the ablation procedure proceeds. If sufficient energy is conducted to the tissue by the conductive media for a sufficient period of time, a satisfactory ablation lesion will be formed.

In order to produce an adequate lesion, the flow of the conductive media should occur through all or substantially all of the openings (116) along the length of the ablation catheter (110). Any structural system which controls the flow of the conductive media through these openings (116) is consistent with this invention. Several such systems are disclosed in application Ser. No. 08/897,300, filed Jul. 21, 1997, which disclosure is incorporated into this application by reference.

Instead of utilizing a coiled electrode (118), as shown in FIG. 6, other electrode systems can be utilized, including a coated tubular body, a conductive filter element, and the utilization of a chemical ablative element. Each of these systems is disclosed in application Ser. No. 08/897,300, filed Jul. 21, 1997, which systems are incorporated by reference into this application.

FIG. 7 discloses another alternative rail catheter ablation and mapping system (200). This system (200) includes a guiding introducer system (11), which is preferably an inner guiding introducer (12) and an outer guiding introducer (14), an ablation catheter (210) and a rail (16). The inner (12) and outer (14) guiding introducers and the rail (16) are similar to those previously discussed. The ablation catheter (210) may have a plurality of electrodes (37). However, no slotted sheath is utilized with this embodiment. The ablation catheter (210) is first extended over the rail (16) to isolate the cardiac tissue from the rail (16). Flushing may be provided through catheter (210) to flow out and around the electrodes (37) for cooling during ablation. In this embodiment, the rail (208) with catheter (210) is then extended from the guiding introducers (12, 14) to circumscribe the chamber of the heart.

In operation, a modified Seldinger technique for inserting hemostasis introducers for vascular access is normally used for the insertion of the associated dilators and hemostasis introducers into the body. The appropriate vessel is accessed by needle puncture. The soft flexible tip of an appropriately sized guidewire is inserted through and a short distance beyond the needle into the vessel. Firmly holding the guidewire in place, the needle is removed. A hemostasis introducer with a dilator is then inserted into the vessel over the guidewire. A long guidewire is then inserted into the vessel through the hemostasis introducer and advanced into the right atrium. A transseptal introducer is then advanced into the right atrium through the hemostasis introducer and over the guidewire. A conventional transseptal technique is used for access into the left atrium of the heart. The guidewire is used to provide a path from the left atrium transseptally back through the hemostasis valve after the transseptal technique has been performed.

Figure 13:
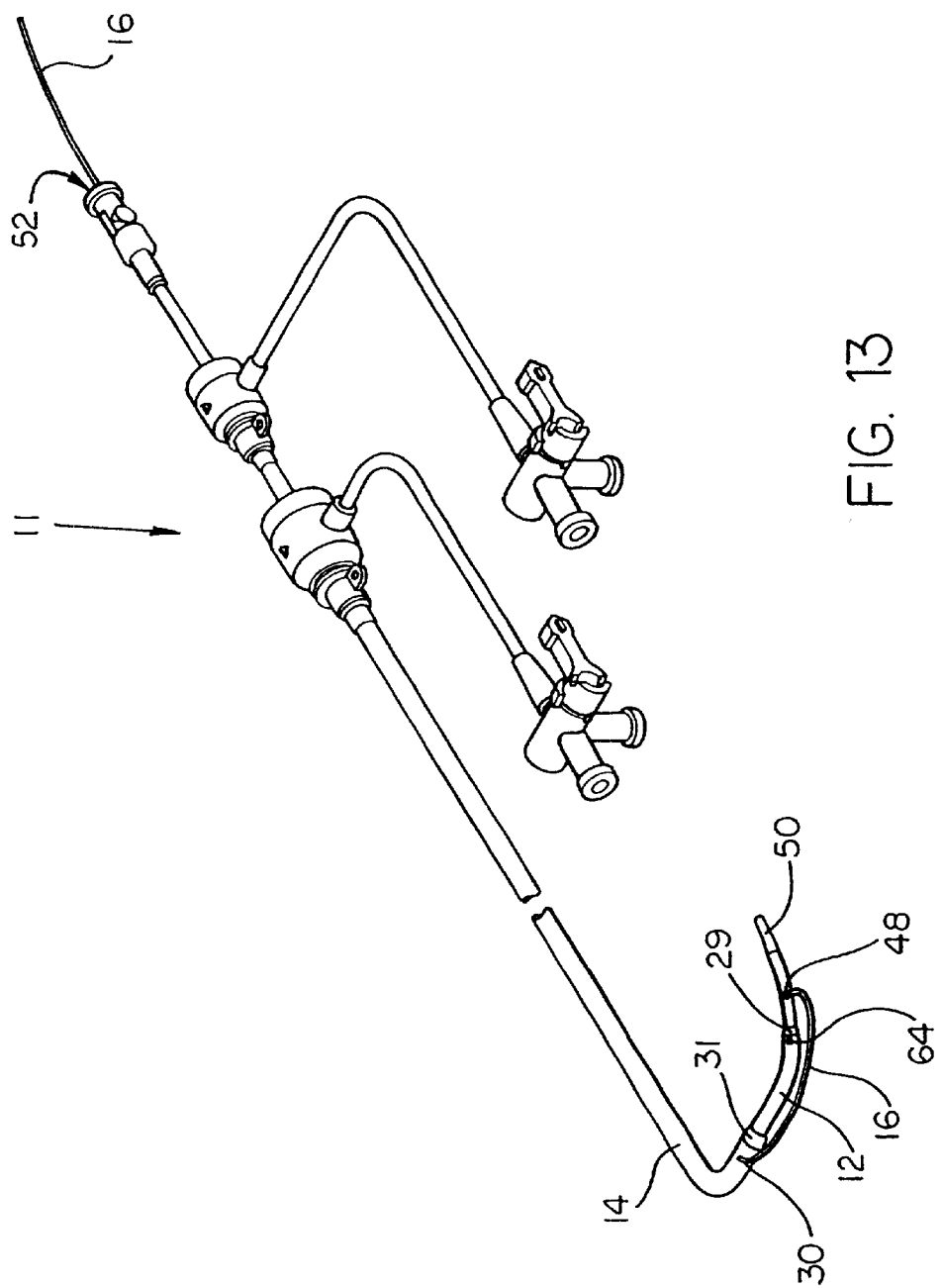
FIG. 13 is a perspective view of the inner and outer guiding introducer system of FIG. 2 with the rail and dilator positioned for vascular introduction.

The system (11), as assembled in FIG. 13, is then introduced over the guidewire. With the guidewire in place, a dilator (50) is advanced over the guidewire within the appropriate inner (12) and outer (14) guiding introducers. The rail (16) exits through the opening (30) in the outer guiding introducer (14) and loops around through an opening (48) in the dilator (50). The rail (16) then extends down the length of the dilator (50) and out its proximal end (52). The dilator (50), inner (12) and outer (14) guiding introducers and rail (16) form an assembly to be advanced together over the guidewire into the appropriate chamber of the heart. After insertion of the assembly into the appropriate chamber of the heart, the guidewire is withdrawn. Once the dilator (50), inner (12) and outer (14) guiding introducers, and rail (16) are in position in the appropriate chamber of the heart, the inner guiding introducer (12) is rotated 180 degrees and the dilator (50) is withdrawn. The slotted sheath (22) of the ablation system (18) is then advanced over the rail (16) into the inner guiding introducer (12). The catheter ablation system (18) is advanced over the rail (16) through the distal tip (29) of the inner guiding introducer (12) until the distal tip (40) of the slotted sheath (22) approaches the opening or slot (30) in the outside surface of the side of the outer guiding introducer (14), as shown in FIGS. 1 and 2. The ablation catheter system (18) is then advanced out of the distal end (29) of the inner guiding introducer (12) such that it contacts the wall of the heart. The distal tip (29) of the inner guiding introducer (12) is advanced away from the distal tip (31) of the outer guiding introducer (14), as shown in FIG. 1, until the distal tip (29) of the inner guiding introducer (12) approaches the opposite side of the chamber of the heart in which the ablation procedure is to be performed. The distal tip (31) of the outer guiding introducer (14) is retained at or near the opening into the chamber of the heart. By this process, a loop of the slotted sheath (22) over the rail (16) can be formed that circumscribes the entire surface of the chamber of the heart as shown in FIG. 1. The specific placement of the ablation system (18) on the surface of the chamber of the heart can be adjusted by rotating, advancing or withdrawing the inner guiding introducer (12) in relation to the outer guiding introducer (14).

After the desired location for ablation is determined, the ablation catheter (20) is positioned within the slotted sheath (22). In a preferred embodiment, as the ablation catheter (20) is advanced, it first senses the electrical activity of that chamber of the heart along the pathway created by the rail (16) located within the slotted sheath (22). Once the proper location for the ablation procedure is determined, the ablation catheter (20) utilizing energy, preferably radiofrequency energy, performs the ablation procedure in the heart and forms a linear lesion by dragging the ablation catheter (20) through the slotted sheath (22). For the catheters (110, 210) the procedure for use is the same as the procedures using the slotted sheath (22). Because of the rail (16), the slotted sheath system (18) or the ablation catheter (110, 210) can maintain tissue contact in the cardiac chamber throughout the ablation procedure, making the formation of linear lesions significantly easier. Thermosensing devices, such as thermocouples, may also be secured to the ablation catheter to determine whether sufficient energy has been applied to the tissue to create an adequate linear lesion.

Alternatively, an ablation catheter can be advanced over the rail (16) to create a linear lesion, such that the rail (16) is in rail (16) to create a linear lesion, such that the rail (16) is in direct contract with the tissue. The rail (16) in this embodiment provides a linear track for the catheter (110, 210) to slide over.

After the ablation procedure is completed, a sensing electrode may be used to determine if the arrhythmia has been eliminated at the particular location within the heart. Additional ablation lesions or tracks may then be produced, if necessary, using the ablation catheter (18, 110, 210) at the same or different locations within the heart.

Pharmacological treatments may also be used in combination with ablation procedures to relieve the atrial arrhythmia.

This rail catheter ablation and mapping system (10, 100, 200, 300) provides several improvements over conventional ablation systems, including steerable catheters. This rail catheter ablation and mapping system (10, 100, 200, 300) allows ablation catheters to maintain positive contact with the cardiac tissue to be ablated to form linear lesions that are contiguous and continuous. These systems also allow the ablation catheter system (18, 110, 210) to be firmly placed against the tissue to be ablated. When used with a guiding introducer system, preferably an inner and outer guiding introducer, a stable platform for the rail and ablation system (18, 110, 210) is created to maintain positive contact with the cardiac tissue to be ablated. The rail catheter ablation and mapping system (10, 100, 200, 300) also permits a single positioning of the ablation catheter for the creation of a linear ablation lesion without the need for continuous repositioning of the ablation catheter. Because the rail is preferably rectangular in shape, it is flexible to conform to the contours of the cardiac tissue to be ablated while still maintaining lateral stiffness to retain the rail catheter ablation and mapping system (10, 100, 200, 300) at the correct location for formation of the linear lesions. The use of a flushing system around the rail and the electrodes prevents formation of coagulum during the ablation procedure.

It will be apparent from the foregoing that while particular forms of the invention have been illustrated and described, various modifications can be made without departing from the spirit and scope of the invention.

What is claimed is:

1. A rail catheter ablation and mapping system for ablation procedures in a chamber of the heart, comprising;

an inner and outer guiding introducer, each containing a lumen, an extendable rail, one end of which is contained within the guiding introducers, wherein the outer guiding introducer contains a slot and wherein the rail extends through the slot in the outer guiding introducer, and an ablation catheter containing a lumen, wherein the catheter passes through the lumen of the inner guiding introducer, and wherein the ablation catheter passes over the rail.

2. The rail catheter ablation and mapping system of claim 1 wherein the rail extends outwardly from the guiding introducer at an angle of about 60 to about 180 degrees.

3. The rail catheter ablation and mapping system of claim 1 wherein the rail has a generally rectangular cross-section.

4. The rail catheter ablation and mapping system of claim 1 wherein one end of the rail is secured to the outer guiding introducer.

5. The rail catheter ablation and mapping system of claim 1 wherein the rail is comprised of a superelastic, shaped memory alloy.

6. The rail catheter ablation and mapping system of claim 1 wherein the ablation catheter further comprises a series of ring electrodes.

7. The rail catheter ablation and mapping system of claim 6 further comprising a system for introducing a cooling fluid through the ablation catheter.

8. The rail catheter ablation and mapping system of claim 6 wherein the ablation catheter is flexible.

9. The rail catheter ablation and mapping system of claim 1 wherein the ablation catheter comprises a plurality of lumens, an electrode contained within one of those lumens and a series of openings in an outer surface of the ablation catheter communicating between the outer surface of the ablation catheter and the electrode.

10. The rail catheter ablation and mapping system of claim 1 wherein the inner and outer guiding introducer containing precurved distal portions.

11. The rail catheter ablation and mapping system of claim 1, wherein the slot forms an opening from about 20 to about 180 degrees around a circumference of the outer guiding introducer.

12. The rail catheter ablation and mapping system of claim 1 further comprising a slotted sheath contained partially within the lumen of the inner guiding introducer, wherein the slotted sheath passes over the rail.

13. The rail catheter ablation and mapping system of claim 12 wherein the slotted sheath comprises a sheath body, a plurality of lumens, a series of openings down a side of the sheath body and an opening in a distal tip of the sheath.

14. The rail catheter ablation and mapping system of claim 13 wherein one of the lumens of the slotted sheath receives the rail.

15. A procedure for mapping and ablation of cardiac tissue comprising preparing an inner outer guiding introducer; each containing a lumen, wherein the outer guiding introducer contains a slot, advancing a rail through at least a portion of the guiding introducers and out through the slot in the outer guiding introducer, advancing the guiding introducers and rail into a chamber of a heart for the mapping and ablating procedure, advancing an ablation catheter through a lumen of the inner guiding introducer into the chamber of the heart, and extending the ablation catheter over the rail inside of the chamber of the heart to map and ablate cardiac tissue with the ablation catheter.

16. A rail catheter ablation and mapping system for ablation procedures in a chamber of the heart comprising;

an inner and outer guiding introducer, each containing a lumen, an extendable rail, one end of which is contained within the guiding introducers, wherein the rail is extendable from the inner and outer guiding introducer, and wherein neither end of the rail is secured to either of the inner or outer introducer, and an ablation cather containing a lumen, wherein the catheter passes through the human of the inner guiding introducer and wherein the ablation catheter passes over the rail.

17. A rail catheter ablation and mapping system for ablation procedures in a chamber of the heart, comprising;

an inner and outer guiding introducer each containing, lumen, an extendable rail, one end of which is contained within the guiding introducers wherein the rail is extendable from the inner and outer proximal end of the outer guiding introducer, and an ablation catheter containing a lumen, wherein the catheter passes through the lumen of the inner guiding introducer and wherein the ablation catheter passes over the rail.

* * * * *